United States Patent [19]

Leistner et al.

[11] 4,450,248
[45] May 22, 1984

[54] HINDERED PIPERIDYL LIGHT STABILIZERS

[75] Inventors: William E. Leistner, Atlantic Beach, N.Y.; Charles G. Overberger, Ann Arbor, Mich.

[73] Assignee: Phoenix Chemical Corporation, Atlantic Beach, N.Y.

[21] Appl. No.: 293,048

[22] Filed: Aug. 14, 1981

Related U.S. Application Data

[63] Continuation of Ser. No. 184,637, Sep. 8, 1980, abandoned.

[51] Int. Cl.³ .................... C08K 5/39; C08F 12/30; C07D 401/00
[52] U.S. Cl. .................... 524/99; 529/102; 528/289; 546/187; 546/188; 546/189; 546/245; 546/323; 546/326
[58] Field of Search ............. 546/187, 188, 189, 245, 546/323, 326; 524/99, 102; 528/289

[56] References Cited

U.S. PATENT DOCUMENTS

| | | | |
|---|---|---|---|
| 2,304,830 | 12/1942 | Katzman | 546/262 |
| 3,334,103 | 8/1967 | Feldman et al. | 546/326 |
| 3,998,784 | 12/1976 | Cook | 524/102 |
| 4,064,102 | 12/1977 | Hillard et al. | 524/102 |
| 4,075,165 | 2/1978 | Soma et al. | 546/188 |
| 4,093,586 | 6/1978 | Stephen | 524/104 |
| 4,104,297 | 8/1978 | Buxbaum et al. | 528/289 |
| 4,111,901 | 9/1978 | Hechenbleikner | 524/104 |
| 4,118,368 | 10/1978 | Soma et al. | 546/187 |
| 4,118,369 | 10/1978 | Minagawa et al. | 524/101 |
| 4,164,480 | 8/1979 | Irick, Jr. et al. | 546/187 |

OTHER PUBLICATIONS

Noller, Chemistry of Organic Compounds, 1958, p. 237.

*Primary Examiner*—John Knight, III
*Assistant Examiner*—Kriellion Morgan

[57] ABSTRACT

Piperidine-4-carboxylic acid derivatives of the formula

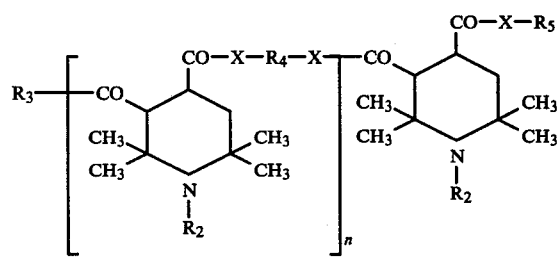

wherein:
$R_2$ is hydrogen, alkyl having from one to four carbon atoms, or oxyl;

$R_3$ is —$XR_5$ or —CN;

$R_4$ is alkylene having from two to twelve carbon atoms; cycloalkylene having from three to twelve carbon atoms; arylene having from six to twelve carbon atoms; or aralkylene having from seven to twelve carbon atoms;

$R_5$ is hydrogen, alkyl having from one to twenty carbon atoms, cycloalkyl having from five to six carbon atoms; or alkenyl having from three to twenty carbon atoms; or

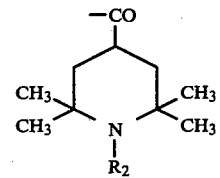

X is —O— or —NH—; and
n is 0 to 10;
and the acid addition salts thereof.

18 Claims, No Drawings

HINDERED PIPERIDYL LIGHT STABILIZERS

This is a continuation of application Ser. No. 184,637, filed Sept. 8, 1980 and now abandoned.

BACKGROUND OF THE INVENTION

Many synthetic organic polymers are degraded by exposure to light resulting in discoloration and/or embrittlement. It is known that actinic radiation, particularly in the near ultraviolet region, has a deleterious effect on the appearance and properties of organic polymers. For example, normally colorless or light colored polyesters and cellulostics such as cellulose acetate yellow on exposure to sun light. Polystyrene discolors and cracks with an accompanying loss of the desirable physical properties when exposed to actinic light, while vinyl resins such as polyvinyl chloride and polyvinyl acetate spot and degrade. The rate of air oxidation of polyolefins such as polyethylene and polypropylene is materially accelerated by ultraviolet light.

Hindered 2,2,6,6-tetraalkyl-4-carboxylic acid ester piperidine compounds were described by Murayama et al in U.S. Pat. No. 3,640,928 as being light and heat stabilizers for synthetic polymers. These compounds have the general formula

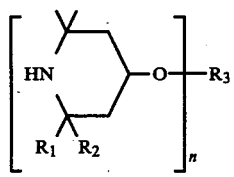

in which $R_1$ and $R_2$ are alkyl or form with the carbon atom to which they are attached a saturated alicyclic group or another piperidine ring, $R_3$ is an acyl group, n is an integer of 1–3 and the salts thereof.

The Murayama compounds have proven to be particularly acceptable because they do not impart a discoloration of their own to the synthetic polymer. The compounds generally employed previously had been either highly colored, such as nickel compounds (normally green) and the 2-hydroxy-benzophenones (varying shades and intensities of yellow). They also showed very little tendency toward sublimation and extrudation, and had an excellent stabilizing action against both heat and light deterioration.

The Murayama et al patent has been followed by a large number of patent and literature disclosures relating to compounds including a 2,2,6,6-tetrasubstituted-4-piperidyl group attached to a base molecule of various structures. Reference can be made, for example, to the following U.S. Pat. Nos. 3,640,928, 3,920,659, 4,064,102, 4,102,858, 4,105,625, and 4,136,081.

Despite the effectiveness of the Murayama type compounds described in the literature the search has continued for new and more effective light stabilizers. It has been desired to realize an enhanced degree of light stabilization and also to obtain stabilizers which are even less likely to exude from the polymeric mass being stabilized.

Hillard et al U.S. Pat. Nos. 4,064,102, teaches esters of the formula

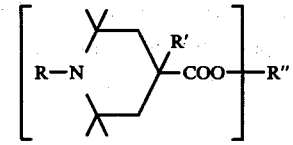

in which R is hydrogen or alkyl, R' is hydrogen, hydroxy, or alkoxy, R" is alkyl, alkylene, cycloalkyl, cycloalkylene, arylene, aralkylene and alkynyl and in which n is an integer from 1 to 4. These esters are stated to provide superior stabilizing properties against photodegradation of synthetic polymers compared to the Murayama type compounds. See also Japan Kokai 77-91,875 and 77-139,071. It is desirable, however, to obtain compounds which have greater stabilizing properties and impair the physical properties to a lesser extent than the Hillard compounds.

It is accordingly the object of this invention to provide new and improved light stabilizers for organic materials which exhibit enhanced light stabilizing properties and/or resistance to exudation from the material being stabilized. This and other objects of the invention will become apparent to those skilled in the art from the following detailed disclosure.

SUMMARY OF THE INVENTION

This invention relates to a hindered piperidyl light stabilizer for organic materials and more particularly to hindered piperidyl light stabilizers of the formula

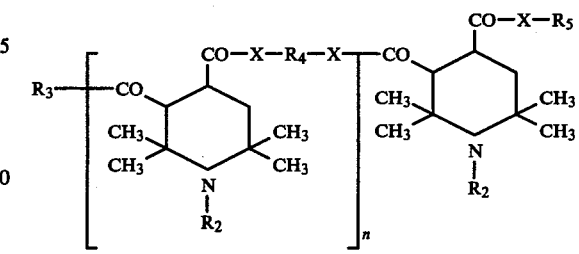

wherein:

$R_2$ is hydrogen, alkyl having from one to four carbon atoms, or oxyl;

$R_3$ is —$XR_5$ or —CN;

$R_4$ is alkylene having from two to twelve carbon atoms; cycloalkylene having from three to twelve carbon atoms; arylene having from six to twelve carbon atoms; or aralkylene having from seven to twelve carbon atoms;

$R_5$ is hydrogen, alkyl having from one to twenty carbon atoms, cycloalkyl having from five to six carbon atoms; or alkenyl having from three to twenty carbon atoms; or

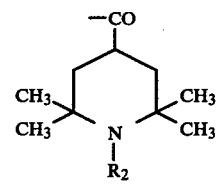

X is —O— or —NH—; and
n is 0 to 10;

and the acid addition salts thereof.

DESCRIPTION OF THE INVENTION

The hindered piperidyl light stabilizers of the present invention are of the formula:

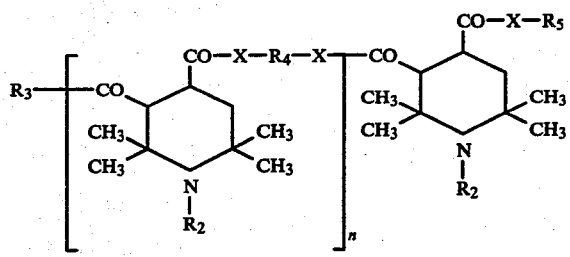

wherein:

$R_2$ is hydrogen, alkyl having from one to four carbon atoms, or oxyl;

$R_3$ is $-XR_5$ or $-CN$;

$R_4$ is alkylene having from two to twelve carbon atoms; cycloalkylene having from three to twelve carbon atoms; arylene having from six to twelve carbon atoms; or aralkylene having from seven to twelve carbon atoms;

$R_5$ is hydrogen, alkyl having from one to twenty carbon atoms, cycloalkyl having from five to six carbon atoms; or alkenyl having from three to twenty carbon atoms; or

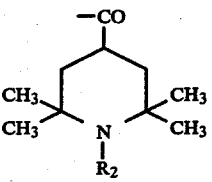

X is $-O-$ or $-NH-$; and n is 0 to 10;

and the acid addition salts thereof. It will be noted that, as distinguished from the Murayama type hindered piperidyl light stabilizers of the prior art, the carbon atom of the acyl radical in the above compounds are connected directly to the 4 carbon atom of the piperidine ring para to the nitrogen.

Any of the alkyl groups can also be hydroxy, epoxy or aryl substituted such as, for example, 2-hydroxyethyl, 2-hydroxypropyl, 2-hydroxybutyl, 2-phenyl-2-hydroxyethyl and 2,3-epoxypropyl.

Typical compounds falling within the scope of the hindered piperidyl light stabilizer formula shown above include

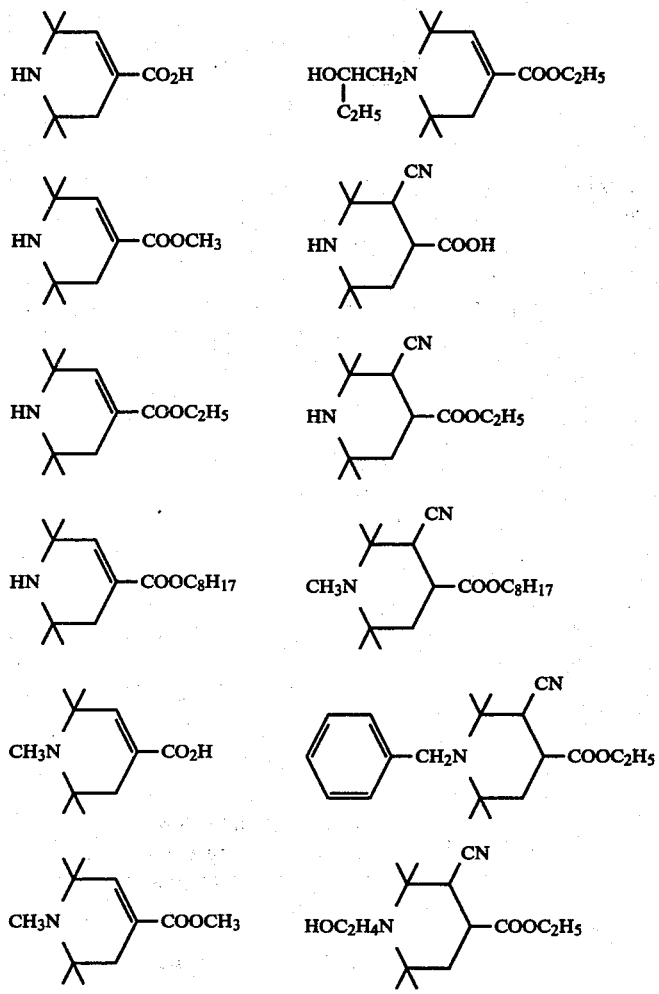

-continued
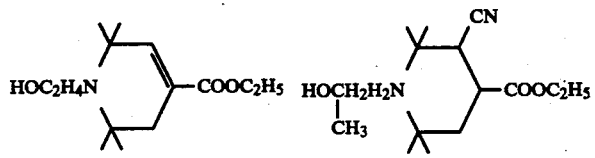
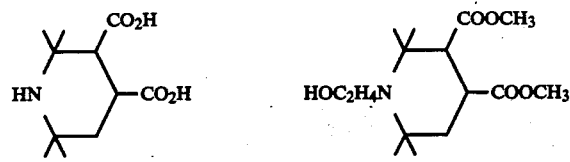
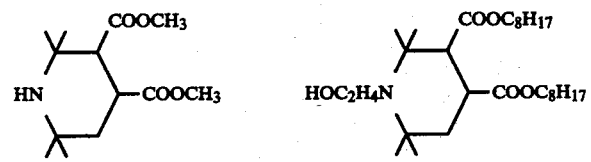
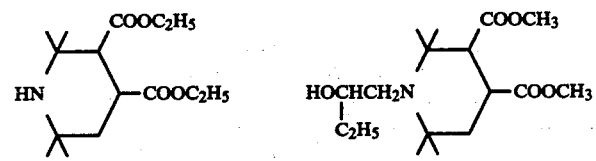
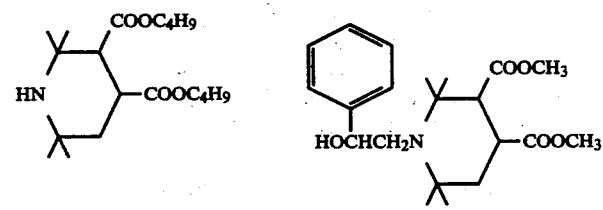
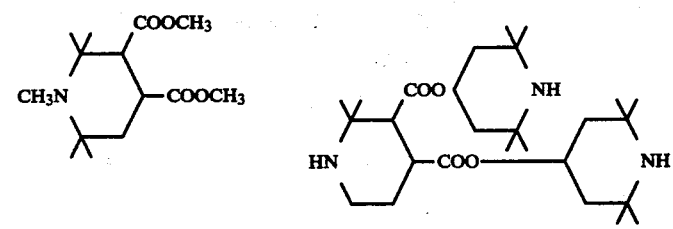
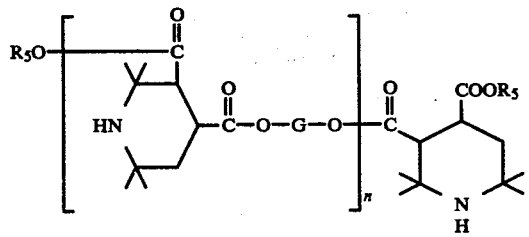
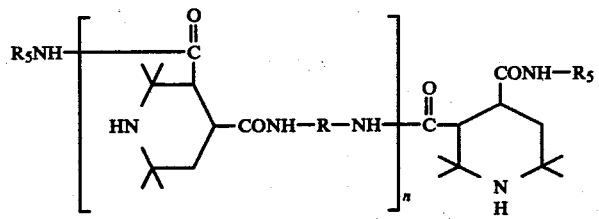

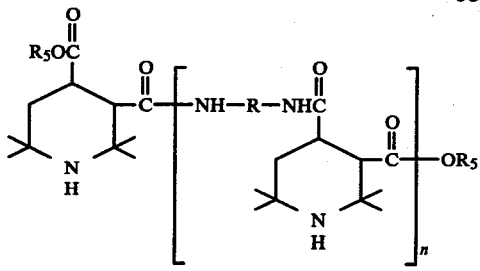

in which G is the residue of a glycol and R is the residue of a diamine.

The hindered piperidyl light stabilizers of the present invention are effective stabilizers which enhance the resistance to deterioration due to heat and/or light of synthetic polymeric materials which are susceptible to such degradation including polyolefins such as low and high density polyethylene, polypropylene, polybutylene, polyisobutylene, polypentylene and polyisopentylene, vinyl polymers such as polystyrene, polydienes such as polybutadiene and polyisoprene, and copolymers of olefins and dienes with other ethylenically and acetylenically unsaturated monomers such as ethylene-propylene copolymers, ethylene-butene copolymers, ethylene-pentene copolymers, ethylene-vinylacetate copolymers, styrene-butadiene copolymers, acrylonitrile-styrene-butadiene copolymerse, synthetic rubbers of all types such as polychloroprene, polyvinyl-halides, including polyvinyl chloride homopolymer, polyvinylidene chloride and copolymers of vinyl chloride and vinylidene chloride, vinyl chloride and vinyl acetate, vinylidene chloride and vinyl acetate, and other ethylenically unsaturated monomers, polyacetyls such as polyoxymethylene and polyoxyethylene, polyesters such as polyethylene glycol-terephthalic acid ester polymers, polyamides such as polyepsiloncaprolactan, polyhexamethylene adipamide and polydecamethylene adipamide, polyurethanes, and epoxy resins.

The synthetic polymer can be in any physical form, including filaments, yarns, films, sheets, molded articles, latexes and foams. The inventive stabilizers can be employed as the sole stabilizer or in combination with other conventional heat and light stabilizers for the particular synthetic polymer. For example, in the case of polyvinyl chloride resins, other polyvinyl chloride resin heat stabilizers can be included, for example, polyvalent metal fatty acid salts such as barium and cadmium salts of the higher fatty acids; organic thiophosphites, organotin compounds; hindered phenols; and epoxy compounds. Fatty acid salts of polyvalent metals, organic phosphites, phenolic antioxidants and the higher fatty acid esters of thiodipropionic acids such as, for example, dilauryl thiodipropionate can be used with polyolefin resins. Similarly, polyamide resin compositions can contain such stabilizers as copper salts in combination with iodides and/or phosphorus compounds and salts of divalent manganese. Synthetic rubbers and acrylonitrile butadiene styrene terpolymers can additionally employ antioxidants such as hindered phenols and bis-phenols, polyvalent metal salts of the higher fatty acids and organic phosphites.

Other conventional additives for synthetic polymers, such as plasticizers, lubricants, emulsifiers, antistatic agents, flame-proofing agents, pigments and fillers, and the like, can also be present.

The new stabilizers are incorporated into the materials to be stabilized in an effective light stabilizing amount. Generally, the compounds will be present in an amount of about 0.001 to 5 weight percent, preferably about 0.01 to 3 weight percent based on the weight of the material to be stabilized.

The inventive compounds can be obtained as the free base or as an acid addition salt with such acids as hydrochloric acid, sulfuric acid, phosphoric acid, hydrobromic acid, p-toluene sulfonic acid, acetic acid and oxalic acid.

The compounds of the present invention can be prepared from 2,2,6,6-tetraalkyl-4-hydroxy-piperidine-4-carboxylic acid which itself can be prepared from acetonecyanohydrin by the procedures described in Hillard Pat. No. 4,064,102. The 3,4 unsaturation is obtained by dehydrating the acid, the 3-cyano group by cyanation and the 3-carboxylic acid group by hydrolysis of the cyano material. The acid functions are converted into esters, amides, etc. by standard esterification, amidation, etc. procedures. These reactions are shown schematically below.

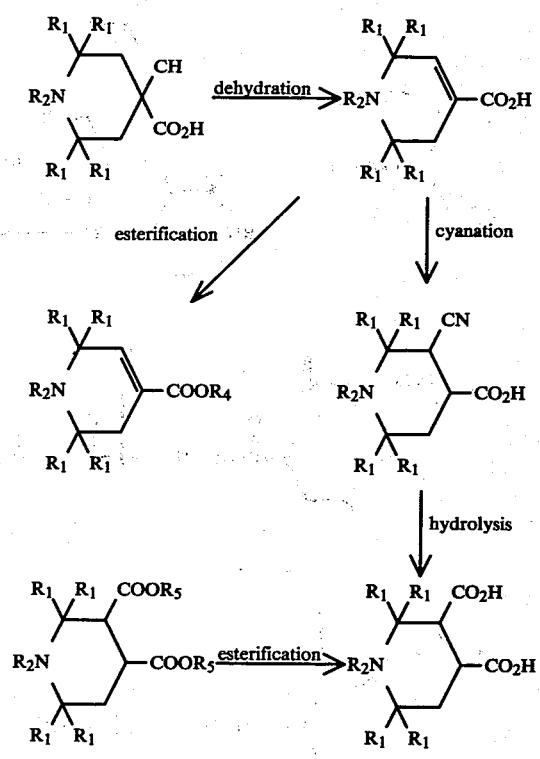

The compounds of the present invention are stabilizers in their own right or are useful in the preparation of stabilizers.

The following examples are presented solely for the purpose of further illustrating the invention but are not intended to limit it.

EXAMPLE 1

2,2,6,6-Tetramethyl-4-piperidone

A solution of 30.8 g acetoneamine 18 g acetone, 5 ml $H_2O$, and 25 g ammonium chloride was heated at reflux for a 13 hour period. The solids were filtered and washes and filtrate were combined and evaporated under vacuum. The remaining viscous liquid was distilled under vacuum to give 28.3 g of the titled product (92%), $b_{15}$ 95°–9° C.

EXAMPLE 2

2,2,6,6-Tetramethyl-4-hydroxy-4-cyanopiperidine

A solution of 97 g 2,2,6,6-tetramethyl-4-piperidone and 67 g of acetone cyanohydrin were stirred at room temperature for 30 hours to precipitate the desired cyanohydrin. The precipitate was collected, washed with petroleum ether and air dried to yield 70 g (61.4%); mp 129°–132° C.

EXAMPLE 3

2,2,6,6-Tetramethyl-4-hydroxy-4-carboethoxypiperidine

The cyanohydrin (10 g) was dissolved in 100 ml of a 10% HCl ethanolic solution and heated at reflux for 5 hours while slowly bubbling dry HCl gas through the reaction mixture. The alcohol was removed by rotary evaporation and the remaining solid dissolved in a 50% aqueous potassium carbonate solution and extracted with several volumes of chloroform. The chloroform extracts were combined, dried, and evaporated to give 10.5 g (80%) of the titled product.

EXAMPLE 4

2,2,6,6-Tetramethyl-4-carboethyoxy-$\Delta^3$-piperidine 2,2,6,6-tetramethyl-4-hydroxy-4-carboethoxypiperidine (22.9 g), 150 ml thionyl chloride, and 150 ml benzene were heated at 70° C. for a 5 hour period. After concentration in vacuum, the residue was dissolved in water, neutralized with a 50% aqueous solution of potassium carbonate, and extracted with several volumes of ether. The ether extracts were combined, dried, and concentrated to a volume of approximately 100 ml. A dry stream of HCl gas was led into the ether solution to precipitate a white powder 20.2 g (81.5%) of 2,2,6,6-tetramethyl-4-carboethoxy-$\Delta^3$-piperidine-HCl; mp 219°–220° C.

EXAMPLE 5

2,2,6,6-Tetramethyl-4-hydroxy-4-carboxypiperidine

A solution of 35 g of the product of Example 2 in 100 ml 12 N HCl was heated at 100° C. for an 8 hour period. The reaction mixture was then evaporated to dryness under vacuum, diluted with 60 ml of 40% NaOH solution, and heated for a 3 hour period. The cooled basic solution was then neutralized with glacial acetic acid to precipitate 31.6 g (81.6%).

EXAMPLE 6

2,2,6,6-Tetramethyl-3-Cyano-4-Carboethyoxypiperidine

One mole of 2,2,6,6-tetramethyl-4-carboethoxy-$\Delta^3$-piperidine hydrochloride was dissolved in ethanol in the presence of an ion exchange resin (IR-400) and about 1.1 moles of acetone cyanohydrin was added. After refluxing for 12 hours, the reaction mixture was cooled, the IR-400 filtered off and the ethanol removed by evaporation to dryness.

The hydrochloride salt is obtained by dissolving the product in tetrahydrofuran and slowly bubbling HCl through the solution.

EXAMPLE 7

2,2,6,6-Tetramethyl-3-Cyano-4-Carboethoxypiperadine

One mole of 2,2,6,6-tetramethyl-4-carboethoxy-$\Delta^3$-piperidine was dissolved in methylene chloride and about 1.1 moles of acetone cyanohydrin added. After stirring for 12 hours, the methylene chloride was removed.

EXAMPLE 8

2,2,6,6-Tetramethyl-3,4-dicarboxypiperadine 2,2,6,6-tetramethyl-3-cyano-4-carboethoxy-piperidine was dissolved in 6 N HCl and heated at about 75° C. for six hours. Benzene was added and the resulting azeotrope with the water and HCl removed at reduced pressure. The product was dissolved in water, passed through a mixed bed resin chromographic column, reduced in volume by vacuum evaporation and the remaining solution freezed dried to give the titled product as a light brown powder. The structure was confirmed by NMR and infrared analysis.

EXAMPLES 9–16

Compositions were prepared using statilizers of the present invention and of the prior art containing 100 parts of polypropylene, 0.2 part of stearyl-$\beta$-3,5-di-tert-butyl-4-hydroxyphenyl propionate and 0.3 of the tested stabilizer. The compositions were thoroughly blended in a Brabender Plastograph and then compression molded to form sheets which were 0.3 mm thick. Pieces of the sheet which were 2.5 cm squares were exposed to a high voltage mercury lamp and the length of time until failure noted. The stabilizers employed and the hours until failure are shown in the following:

TABLE 1

| Example | Stabilizer | Hours to Failure |
|---|---|---|
| Control | Methyl 2,2,6,6-tetramethyl-piperidine-4-carboxylate | 360 |
| Control | 2,2,6,6-tetramethyl-4-piperidyl acetate | 360 |
| 9 | 2,2,6,6-tetramethyl-4-carbomethoxy-$\Delta$-3-piperidine | 520 |
| 10 | 2,2,6,6-tetramethyl-4-carboethoxy-$\Delta$-3-piperidine | 540 |
| 11 | 1,2,2,6,6-pentamethyl-4-carbomethoxy-$\Delta$-3-piperidine | 520 |
| 12 | 2,2,6,6-tetramethyl-3-cyano-4-carboethoxy piperidine | 550 |
| 13 | 2,2,6,6-tetramethyl-1-hydroxyethyl-3-cyano-4-carboethoxy piperidine | 560 |
| 14 | 2,2,6,6-tetramethyl-3,4-di-carbomethoxy piperidine | 590 |
| 15 | Bis(2',2',6',6'-teramethyl-4'-piperidyl)-2,2,6,6-tetramethyl-piperidine-3,4-di-carboxylate | 740 |

TABLE 1-continued

| Example | Stabilizer | Hours to Failure |
|---|---|---|
| 16 | CH₃O—[C(O)—[piperidine]—COC₂H₄O]₆—C(O)—[piperidine]—COCH₃ | 680 |

EXAMPLES 17-24

Polyurethane compositions were prepared employing stabilizers of the present invention and of the prior art by mixing 0.3 part of the tested stabilizer with a urethane composition containing 100 parts of a polyurethane resin made from toluene diisocyanate and poly-1,4-butyleneglycol adipate, 0.7 part calcium stearate, 0.3 part zinc stearate and 0.1 part 2,6-di-t-butyl-p-cresol on a two roll mill for 5 minutes at 70° C. Sheets 0.5 mm thick were compression molded at 120° C. for five minutes. The sheets were cut into 2.5 cm squares and exposed to ultraviolet light in a Weather-O-Meter for 30 hours. The tensile strength both before and after exposure was measured. The stabilizer employed and the percentage of tensile strength retained after exposure is set forth in Table II:

TABLE II

| Example | Stabilizer | % Retention of Tensile Strength |
|---|---|---|
| Control | Methyl 2,2,6,6-tetramethylpiperidine-4-carboxylate | 52 |
| Control | 2,2,6,6-tetramethyl-4-piperidyl acetate | 47 |
| 17 | 2,2,6,6-tetramethyl-4-carbomethoxy-Δ3-piperidine | 68 |
| 18 | 2,2,6,6-tetramethyl-1-hydroxyethyl-4-carboethoxy-Δ3-piperidine | 65 |
| 19 | 2,2,6,6-tetramethyl-3-cyano-4-carboethoxypiperidine | 71 |
| 20 | 1,2,2,6,6-pentamethyl-3-cyano-4-carbooctoxy piperidine | 67 |
| 21 | 2,2,6,6-tetramethyl-3,4-di-carbomethoxypiperidine | 73 |
| 22 | Bis(2',2',6',6'-tetramethyl-4'-piperidyl)-2,2,6,6-tetramethyl-piperidine-3,4-di-carboxylate | 80 |
| 23 | CH₃O—[C(O)—[piperidine]—COC₂H₄O]₆—C(O)—[piperidine]—COCH₃ | 80 |
| 24 | CH₃O—[C(O)—[piperidine]—COCH₂C(CH₃)₂—CH₂O]₄—C(O)—[piperidine]—COCH₃ | 82 |

Various changes and modifications can be made in the invention without departing from the spirit and scope of the invention. The various embodiments of the invention disclosed herein serve to further illustrate the invention, but are not intended to limit it.

What is claimed is:

1. A piperidine-4-carboxylic acid derivative of the formula

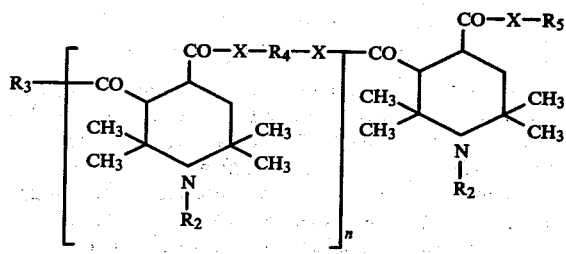

wherein:
$R_2$ is hydrogen, alkyl having from one to four carbon atoms, or oxyl;
$R_3$ is —$XR_5$ or —CN;
$R_4$ is alkylene having from two to twelve carbon atoms; cycloalkylene having from three to twelve carbon atoms; arylene having from six to twelve carbon atoms; or aralkylene having from seven to twelve carbon atoms;
$R_5$ is hydrogen, alkyl having from one to twenty carbon atoms, cycloalkyl having from five to six carbon atoms; or alkenyl having from three to twenty carbon atoms; or

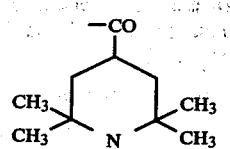

X is —O— or —NH—; and n is 0 to 10;

and the acid addition salts thereof.

2. The derivative of claim 1, wherein $R_3$ is —CN.

3. The derivative of claim 2, wherein $R_2$ is hydrogen or alkyl, $R_5$ is hydrogen or alkyl, X is —O—, and n is 0.

4. The derivative of claim 3, wherein $R_2$ is hydrogen.

5. The derivative of claim 1, wherein $R_3$ is —$XR_5$.

6. The derivative of claim 5, wherein $R_2$ is hydrogen or alkyl, and $R_5$ is hydrogen, alkyl or

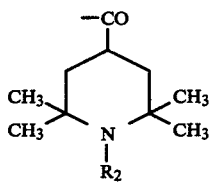

7. The derivative of claim 6, wherein X is —O—.

8. Bis(2',2',6',6'-tetramethyl-4'-piperidyl)-2,2,6,6-tetramethyl-piperidine-3,4-di-carboxylate in accordance with claim 7.

9.

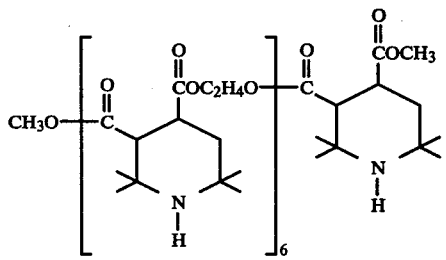

in accordance with claim 7.

10. A composition comprising a light degradable synthetic organic polymer and the piperidine-4-carboxylic acid derivative of claim 1.

11. A composition comprising a light degradable synthetic organic polymer and the piperidine-4-carboxylic acid derivative of claim 2.

12. A composition comprising a light degradable synthetic organic polymer and the piperidine-4-carboxylic acid derivative of claim 3.

13. A composition comprising a light degradable synthetic organic polymer and the piperidine-4-carboxylic acid derivative of claim 4.

14. A composition comprising a light degradable synthetic organic polymer and the piperidine-4-carboxylic acid derivative of claim 5.

15. A composition comprising a light degradable synthetic organic polymer and the piperidine-4-carboxylic acid derivative of claim 6.

16. A composition comprising a light degradable synthetic organic polymer and the piperidine-4-carboxylic acid derivative of claim 7.

17. A composition comprising a light degradable synthetic organic polymer and the piperidine-4-carboxylic acid derivative of claim 8.

18. A composition comprising a light degradable synthetic organic polymer and the piperidine-4-carboxylic acid derivative of claim 9.

* * * * *